United States Patent [19]

Hanson et al.

[11] Patent Number: 5,432,201
[45] Date of Patent: Jul. 11, 1995

[54] ALKYLAMINOALKYL-SULFONYL-TERMINATED β-ALANINEAMIDE AMINO-DIOL COMPOUNDS FOR TREATMENT OF HYPERTENSION

[75] Inventors: Gunnar J. Hanson, Skokie; John S. Baran, Winnetka; Barbara B. Chen, Glenview, all of Ill.

[73] Assignee: G. D. Searle & Co., Chicago, Ill.

[21] Appl. No.: 157,344

[22] Filed: Nov. 22, 1993

[51] Int. Cl.[6] .................. A61K 31/16; A61K 31/165; C07C 323/41
[52] U.S. Cl. ..................... 514/616; 564/154
[58] Field of Search .......... 564/154; 514/616

[56] References Cited

U.S. PATENT DOCUMENTS

| | | | |
|---|---|---|---|
| 5,246,969 | 9/1993 | Hanson et al. | 514/616 |
| 5,268,391 | 12/1993 | Hanson et al. | 514/616 |
| 5,312,838 | 5/1994 | Chen et al. | 514/616 |
| 5,314,920 | 5/1994 | Chen et al. | 514/616 |

*Primary Examiner*—Richard L. Raymond
*Attorney, Agent, or Firm*—J. Timothy Keane

[57] ABSTRACT

Compounds characterized generally as alkylaminoalkyl-terminated β-alanineamide amino diol derivatives are useful as renin inhibitors for the treatment of hypertension. Compounds of particular interest are those of the formula

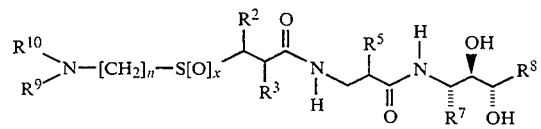

wherein n is two or three; wherein x is a number selected from zero, one and two; wherein $R^2$ is selected from hydrido, methyl, ethyl and phenyl; wherein $R^3$ is selected from hydrido, cyclohexylmethyl, benzyl, fluorobenzyl, chlorobenzyl, napthylmethyl, fluoronaphthylmethyl and chloronaphthylmethyl; wherein $R^5$ is methyl; wherein $R^7$ is cyclohexylmethyl; wherein $R^8$ is selected from n-propyl, isobutyl, cyclopropyl, cyclopropylmethyl, allyl and vinyl; and wherein each of $R^9$ and $R^{10}$ is a group independently selected from methyl, ethyl and isopropyl; or a pharmaceutically-acceptable salt thereof.

30 Claims, No Drawings

ALKYLAMINOALKYL-SULFONYL-TERMINATED β-ALANINEAMIDE AMINO-DIOL COMPOUNDS FOR TREATMENT OF HYPERTENSION

FIELD OF THE INVENTION

Renin-inhibiting compounds are known for control of hypertension. Of particular interest herein are compounds useful as renin inhibiting agents.

BACKGROUND OF THE INVENTION

Renin is a proteolytic enzyme produced and secreted into the bloodstream by the juxtaglomerular cells of the kidney. In the bloodstream, renin cleaves a peptide bond in the serum protein angiotensinogen to produce a decapeptide known as angiotensin I. A second enzyme known as angiotensin converting enzyme, cleaves angiotensin I to produce the octapeptide known as angiotensin II. Angiotensin II is a potent pressor agent responsible for vasoconstriction and elevation of cardiovascular pressure. Attempts have been made to control hypertension by blocking the action of renin or by blocking the formation of angiotensin II in the body with inhibitors of angiotensin I converting enzyme.

Classes of compounds published as inhibitors of the action of renin on angiotensinogen include renin antibodies, pepstatin and its analogs, phospholipids, angiotensinogen analogs, pro-renin related analogs and peptide aldehydes.

A peptide isolated from actinomyces has been reported as an inhibitor of aspartyl proteases such as pepsin, cathepsin D and renin [Umezawa et al, in *J. Antibiot. (Tokyo)*, 23, 259-262 (1970)]. This peptide, known as pepstatin, was found to reduce blood pressure in vivo after the injection of hog renin into nephrectomized rats [Gross et al, *Science*, 175, 656 (1971)]. Pepstatin has the disadvantages of low solubility and of inhibiting acid proteases in addition to renin. Modified pepstatins have been synthesized in an attempt to increase the specificity for human renin over other physiologically important enzymes. While some degree of specificity has been achieved, this approach has led to rather high molecular weight hepta- and octapeptides [Boger et al, *Nature*, 303, 81 (1983)]. High molecular weight peptides are generally considered undesirable as drugs because gastrointestinal absorption is impaired and plasma stability is compromised.

Short peptide aldehydes have been reported as renin inhibitors [Kokubu et al, *Biochim. Biophys. Res. Commun.*, 118, 929 (1984); Castro et al, *FEBS Lett.*, 167, 273 (1984)]. Such compounds have a reactive C-terminal aldehyde group and would likely be unstable in vivo.

Other peptidyl compounds have been described as renin inhibitors. EP Appl. #128,762, published 18 Dec. 1984, describes dipeptide and tripeptide glyco-containing compounds as renin inhibitors [also see Hanson et al, *Biochm. Biophys. Res. Comm.*, 132, 155-161 (1985), 146, 959-963 (1987)]. EP Appl. #181,110, published 14 May 1986, describes dipeptide histidine derivatives as renin inhibitors. EP Appl. #186,977 published 9 Jul. 1986 describes renin-inhibiting compounds containing an alkynyl moiety, specifically a propargyl glycine moiety, attached to the main chain between the N-terminus and the C-terminus, such as N-[4(S)-[(N)-[bis(1-naphthylmethyl)acetyl]-D,L-propargylglycylamino]-3(S)-hydroxy-6-methylheptanoyl]-L-isoleucinol. EP Appl. #189,203, published 30 Jul. 1986, describes peptidyl-aminodiols as renin inhibitors. EP Appl. #200,406, published 10 Dec. 1986, describes alkylnaphthylmethylpropionylhistidyl aminohydroxy alkanoates as renin inhibitors. EP Appl. #216,539, published 1 Apr. 1987, describes alkylnaphthylmethylpropionyl aminoacyl aminoalkanoate compounds as renin inhibitors orally administered for treatment of renin-associated hypertension. PCT Application No. WO 87/04349, published 30 Jul. 1987, describes aminocarbonyl aminoacyl hydroxyether derivatives having an alkylamino-containing terminal substituent and which are described as having renin-inhibiting activity for use in treating hypertension. EP Appl. #300,189 published 25 Jan. 1989 describes amino acid monohydric derivatives having an alkylaminoalkylamino N-terminus and a β-alanine-histidine or sarcosyl-histidine attached to the main chain between the N-terminus and the C-terminus, which derivatives are mentioned as useful in treating hypertension. U.S. Pat. No. 4,902,706 which issued 13 Feb. 1990 describes a series of histidineamide-containing amino alkylaminocarbonyl-N-terminal aminodiol derivatives for use as renin inhibitors. U.S. Pat. No. 5,032,577 which issued 16 Jul. 1991 describes a series of histidineamideaminodiol-containing renin inhibitors.

Several classes of sulfonyl-containing aminodiol renin-inhibitor compounds are known. For example, EP #229,667 published 22 Jul. 1987 describes generally alkylsulfonyl histidineamide amino diol C-terminated-alkyl compounds as renin inhibitors. Australian Pat. Application #30797/89 published 7 Sep. 1989 describes alkylsulfonyl histineamide amino diol C-terminated-alkyl compounds as renin inhibitors, such as (S)-α-[(S)-α-[(t-butyl-sulphonyl)methyl]hydrocinnamamido]-N-[(1S,2R,3RS)-1-(cyclohexylmethyl)-2,3-dihydroxy-4,4-dimethylpentyl]-imidazole-4-propionamide and (S)-α-[(S)-α-[(t-butylsulphonyl)methyl]hydrocinnamamido]-N-[(1S,2R,3S,4RS)-1-(cyclohexylmethyl)-2,3-dihydroxy-4-methylhexyl]imidazole-4-propionamide. U.S. Pat. No. 4,914,129 issued 3 Apr. 1990 describes sulfone-containing amino-hydroxyvaleryl compounds for use as antihypertensive agents, such as the compounds N-[2(S)-benzyl-3-tert-methylsulfonylpropionyl]-His-Cha-Val-n-butylamide and N-[2 (R)-benzyl-3-tert-methylsulfonylpropionyl]-His-Cha-Val-n-butylamide. EP #416,373 published 13 Mar. 91 describes alkylsulfonyl histidineamide amino diol compounds as renin-inhibitors, such as (S)-α-[(S)-α-[(tert-butylsulfonyl)methyl]-hydrocinnamamido]-N-[(1S,2R,3S)-1-(cyclohexylmethyl)-3-cyclopropyl-2,3-dihydroxypropyl]-imidazol-4-propionamide and (S)-α-[(S)-α-[(tert-butylsulfonyl)methyl]-hydrocinnamamido]-N-[(1S,2R,3R/S)-1-(cyclohexylmethyl)-3-cyclopropyl-2,3-dihydroxybutyl-]imidazol-4-propionamide.

Alkylaminoalkyl-terminated amino-diol renin-inhibitor compounds are known. For example, U.S. Pat. No. 4,900,745 to Hanson et al which issued 13 Feb. 1990 describes poly(aminoalkyl)aminocarbonyl amino-diol amino acid derivatives as antihypertensive agents such as O-{N-[2-{N-[2-(N,N-dimethylamino)ethyl]-N-methylamino}-ethyl]-N-methylaminocarbonyl}-3-L-homophenyllactyl-α-(R)-ethyl-β-alanineamide of (2S,3R,4S)-2-amino-1-cyclohexyl-3,4-dihydroxy-6-methylheptane and O-{N-[2-{N-[2-(N,N-dimethylamino)ethyl]-N-methylamino}-ethyl]-N-methylaminocarbonyl}-3-L-phenyllactyl-L-leucineamide of (2S,3R,4S)-2-amino-1-cyclohexyl-3,4-dihydroxy-6-methylheptane. U.S. Pat. No. 4,902,706 to Hanson et al which issued 20 Feb. 1990 describes aminoalkylaminocarbonyl amino-diol amino acid derivatives as antihypertensive agents such as O-{N-[2-(N,N-dimethylamino)ethyl]-N-methylaminocarbonyl}-3-L-homophenyllactyl-α-(R)-ethyl-β-alanineamide of (2S,3R,4S)-2-amino-1-cyclohexyl-3,4-dihydroxy-6-methylheptane and O-{N-[2-(N,N-dimethylamino)ethyl]-N-methylaminocarbonyl-3-L-phenyllactyl-L-leucineamide of (2S,3R,4S)-2-amino-1-cyclohexyl-3,4-dihydroxy-6-methylheptane.

Beta-amino-acid-containing amino-diol compounds have been described as renin inhibitors. For example, U.S. Pat. No. 4,900,746 to Hanson et al which issued 13 Feb. 1990 describes ethereal N-terminal aminodiol amino acid derivatives as antihypertensive agents such as O-[N-methyl-N-(2-methoxyethyl)aminocarbonyl]-3-L-homophenyllactyl-α-(R)-methyl-β-alanineamide of (2S,3R,4S)-2-amino-1-cyclohexyl-3,4-dihydroxy-6-methylheptane. U.S. Pat. No. 4,931,429 which issued 5 Jun. 1990 describes α-aminoacyl-β-aminoacyl aminodiols as antihypertensive agents such as Boc-L-phenylalaninyl-D,L-α-methyl-β-alanineamide of (2S,3R,4S)-2-amino-1-cyclohexyl-3,4-dihydroxy-6-methylheptane. U.S. Pat. No. 5,089,471 which issued 18 Feb. 1992 describes peptidyl β-aminoacyl aminodiol carbamates as antihypertensive agents such as O-(N-morpholinocarbonyl)-3-L-phenyllactyl-α-(R)-methyl-β-alaninamide of (2S,3R,4S)-2-amino-1-cyclohexyl-3,4-dihydroxy-6methylheptane.

DESCRIPTION OF THE INVENTION

Alkylaminoalkyl-sulfonyl-terminated β-alanine amino diol compounds, having utility as renin inhibitors for treatment of hypertension in a subject, constitute a family of compounds of general Formula I:

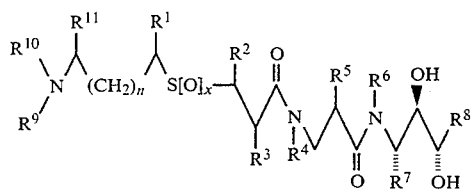

wherein each of $R^1$ and $R^{11}$ is a group independently selected from hydrido, alkyl, alkylaminoalkyl and phenyl; wherein n is a number selected from zero through five, inclusive; wherein x is a number selected from zero, one and two; wherein $R^2$ is selected from hydrido and alkyl; wherein $R^3$ is a group selected from hydrido, cycloalkylalkyl, aralkyl and haloaralkyl; wherein each of $R^4$ and $R^6$ is a group independently selected from hydrido and methyl; wherein $R^5$ is selected from linear and branched alkyl groups containing from one to about four carbon atoms; wherein $R^7$ is a group selected from alkyl, cycloalkylalkyl and aralkyl; wherein $R^8$ is a group selected from hydrido, alkyl, hydroxyalkyl, cycloalkyl, cycloalkylalkyl, alkenyl and haloalkenyl; wherein each of $R^9$ and $R^{10}$ is a group independently selected from hydrido, alkyl, cycloalkyl, cycloalkylalkyl, alkylacyl, aryl, aralkyl, haloaryl and haloaralkyl; and wherein any one of said $R^1$ through $R^{11}$ groups having a substitutable position may be substituted with one or more groups selected from alkyl, hydroxy, hydroxyalkyl, halos alkoxy, alkoxyalkyl and alkenyl; or a pharmaceutically-acceptable salt thereof.

A preferred family of compounds consists of compounds of Formula I wherein each of $R^1$ and $R^{11}$ is independently selected from hydrido, methyl, ethyl, n-propyl, isopropyl, n-butyl, sec-butyl, iso-butyl, tert-butyl, N,N-dimethylaminomethyl, N,N-diethylaminomethyl, N,N-diethylaminoethyl and phenyl; wherein n is a number selected from zero through four, inclusive; wherein x is a number selected from zero, one and two; wherein $R^2$ is selected from hydrido and alkyl; wherein $R^3$ is selected from hydrido, cycloalkylalkyl, phenylalkyl, halophenylalkyl, naphthylalkyl and halonaphthylalkyl; wherein each of $R^4$ and $R^6$ is independently selected from hydrido and methyl; wherein $R^5$ is selected from methyl, ethyl, n-propyl, isopropyl and n-butyl; wherein $R^7$ is selected from cyclohexylmethyl and benzyl, either one of which may be substituted with one or more groups selected from alkyl, hydroxy and alkoxy; wherein $R^8$ is selected from hydrido, alkyl, cycloalkyl, cycloalkylalkyl, hydroxyalkyl, alkenyl and haloalkenyl; and wherein each of $R^9$ and $R^{10}$ is independently selected from hydrido, alkyl, cycloalkyl, cycloalkylalkyl, alkanoyl, halophenyl, phenylalkyl, halophenylalkyl, naphthyl, halonaphthyl, naphthylalkyl and halonaphthylalkyl; or a pharmaceutically-acceptable salt thereof.

A more preferred family of compounds consists of compounds of Formula I wherein each of $R^1$ and $R^{11}$ is independently selected from hydrido, methyl, ethyl, n-propyl and isopropyl; wherein n is a number selected from zero through three, inclusive; wherein x is a number selected from zero, one and two; wherein $R^2$ is selected from hydrido, methyl, ethyl and n-propyl; wherein $R^3$ is selected from hydrido, cyclohexylmethyl, benzyl, phenylethyl, fluorobenzyl, fluorophenylethyl, chlorobenzyl, chlorophenylethyl, naphthylmethyl, naphthylethyl, fluoronaphthylmethyl and chloronaphthylmethyl; wherein each of $R^4$ and $R^6$ is independently selected from hydrido and methyl; wherein $R^5$ is selected from methyl, ethyl, n-propyl and isopropyl; wherein $R^7$ is cyclohexylmethyl; wherein $R^8$ is selected from methyl, ethyl, n-propyl, isopropyl, n-butyl, isobutyl, sec-butyl, tert-butyl, cyclopropyl, cyclobutyl, cyclopropylmethyl, cyclobutylmethyl, cyclohexylmethyl, allyl and vinyl; and wherein each of $R^9$ and $R^{10}$ is independently selected from hydrido, methyl, ethyl, n-propyl, isopropyl, n-butyl, isobutyl, sec-butyl, tert-butyl, cyclopropyl, cyclopropylmethyl, cyclopropylethyl, propylcarbonyl, ethylcarbonyl, methylcarbonyl, phenyl, benzyl, phenylethyl, monochlorophenyl, dichlorophenyl, monofluorophenyl, difluorophenyl, monochlorophenylmethyl, monochlorophenylethyl, dichlorophenylmethyl, dichlorophenylethyl, naphthyl, monofluoronaphthyl, monochloronaphthyl, naphthylmethyl, naphthylethyl, fluornapthylmethyl and chloronaphthylethyl; or a pharmaceutically-acceptable salt thereof.

An even more preferred family of compounds consists of compounds Formula I wherein each of $R^1$ and $R^{11}$ is independently hydrido or methyl; wherein n is a number selected from zero through three, inclusive; wherein x is zero or two; wherein $R^2$ is selected from hydrido, methyl, ethyl and n-propyl; wherein $R^3$ is selected from hydrido, cyclohexylmethyl, benzyl, phenylethyl, phenylpropyl, fluorobenzyl, fluorophenylethyl, chlorobenzyl, chlorophenylethyl, naphthylmethyl, naphthylethyl, fluoronaphthylmethyl and chloronaphthylmethyl; wherein each of $R^4$ and $R^6$ is hydrido; wherein $R^5$ is selected from methyl and ethyl; wherein $R^7$ is cyclohexylmethyl; wherein $R^8$ is selected from ethyl, n-propyl, n-butyl, isobutyl, cyclopropyl, cyclobutyl, cyclopropylmethyl, allyl and vinyl; wherein each of $R^9$ and $R^{10}$ is independently selected from hydrido, methyl, ethyl, n-propyl, isopropyl, cyclopropylmethyl, phenyl, benzyl, monochlorophenyl and dichlorophenyl; or a pharmaceutically-acceptable salt thereof.

A highly preferred family of compounds consists of compounds of Formula II:

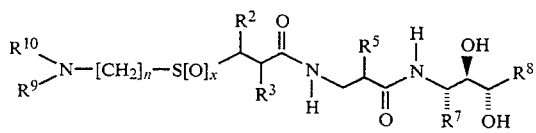

wherein n is two or three; wherein x is a number selected from zero, one and two; wherein $R^2$ is selected from hydrido, methyl, ethyl and phenyl; wherein $R^3$ is selected from hydrido, cyclohexylmethyl, benzyl, fluorobenzyl, chlorobenzyl, fluoronaphthylmethyl, naphthylmethyl and chloronaphthylmethyl; wherein $R^7$ is cyclohexylmethyl; wherein $R^8$ is selected from n-propyl, isobutyl, cyclopropyl, cyclopropylmethyl, allyl and vinyl; wherein each of $R^9$ and $R^{10}$ is independently selected from methyl, ethyl and isopropyl; or a pharmaceutically-acceptable salt thereof.

The term "hydrido" denotes a single hydrogen atom (H). This hydrido group may be attached, for example, to an oxygen atom to form a hydroxyl group; or, as another example, one hydrido group may be attached to a carbon atom to form a

group; or, as another example, two hydrido groups may be attached to a carbon atom to form a —CH$_2$-group. Where the term "alkyl" is used, either alone or within other terms such as "hydroxyalkyl", the term "alkyl" embraces linear or branched radicals having one to about twenty carbon atoms or, preferably, one to about twelve carbon atoms. More preferred alkyl radicals are "lower alkyl" radicals having one to about ten carbon atoms. Most preferred are lower alkyl radicals having one to about six carbon atoms. The term "cycloalkyl" embraces cyclic radicals having three to about ten ring carbon atoms, preferably three to about six carbon atoms, such as cyclopropyl, cyclobutyl, cyclopentyl and cyclohexyl. The terms "alkylol" and "hydroxyalkyl" embrace linear or branched alkyl groups having one to about ten carbon atoms any one of which may be substituted with one or more hydroxyl groups. The term "alkenyl" embraces linear or branched radicals having two to about twenty carbon atoms, preferably three to about ten carbon atoms, and containing at least one carbon-carbon double bond, which carbon-carbon double bond may have either cis or trans geometry within the alkenyl moiety. The terms "alkoxy" and "alkoxyalkyl" embrace linear or branched oxy-containing radicals each having alkyl portions of one to about ten carbon atoms, such as methoxy group. The term "alkoxyalkyl" also embraces alkyl radicals having two or more alkoxy groups attached to the alkyl radical, that is, to form monoalkoxyalkyl and dialkoxyalkyl groups. Preferred aryl groups are those consisting of one, two, or three benzene rings. The term "aryl" embraces aromatic radicals such as phenyl, naphthyl and biphenyl. The term "aralkyl" embraces aryl-substituted alkyl radicals such as benzyl, diphenylmethyl, triphenylmethyl, phenyl-ethyl, phenylbutyl and diphenylethyl. The terms "benzyl" and "phenylmethyl" are interchangeable. Each of the terms sulfide, sulfinyl, and "sulfonyl", whether used alone or linked to other terms, denotes, respectively, the divalent radicals

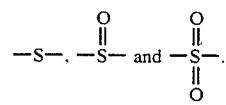

The term "alkenylalkyl" denotes a radical having a double-bond unsaturation site between two carbons, and which radical may consist of only two carbons or may be further substituted with alkyl groups which may optionally contain additional double-bond unsaturation. For any of the foregoing defined radicals, preferred radicals are those containing from one to about fifteen carbon atoms.

Specific examples of alkyl groups are methyl, ethyl, n-propyl, isopropyl, n-butyl, sec-butyl, isobutyl, tert-butyl, n-pentyl, isopentyl, methylbutyl, dimethylbutyl and neopentyl. Typical alkenyl and alkynyl groups may have one unsaturated bond, such as an allyl group, or may have a plurality of unsaturated bonds, with such plurality of bonds either adjacent, such as allene-type structures, or in conjugation, or separated by several saturated carbons.

Also included in the family of compounds of Formula I are isomeric forms, including diastereoisomers. Compounds of Formula I would be useful to treat various circulatory-related disorders. As used herein, the term "circulatory-related" disorder is intended to embrace cardiovascular disorders and disorders of the circulatory system, as well as disorders related to the circulatory system such as ophthalmic disorders including glaucoma. In particular, compounds of Formula I would be useful to inhibit enzymatic conversion of angiotensinogen to angiotensin I. When administered orally, a compound of Formula I would be expected to inhibit plasma renin activity and, consequently, lower blood pressure in a patient such as a mammalian subject (e.g., a human subject). Thus, compounds of Formula I would be therapeutically useful in methods for treating hypertension by administering to a hypertensive subject a therapeutically-effective amount of a compound of Formula I. The phrase "hypertensive subject" means, in this context, a subject suffering from or afflicted with the effects of hypertension or susceptible to a hypertensive condition if not treated to prevent or control such hypertension. Other examples of circulatory-related disorders which could be treated by compounds of the invention include congestive heart failure, renal failure and glaucoma.

Description of the Synthetic Methods for the
Preparation of the Renin Inhibitors of the
Invention Synthetic Scheme 1

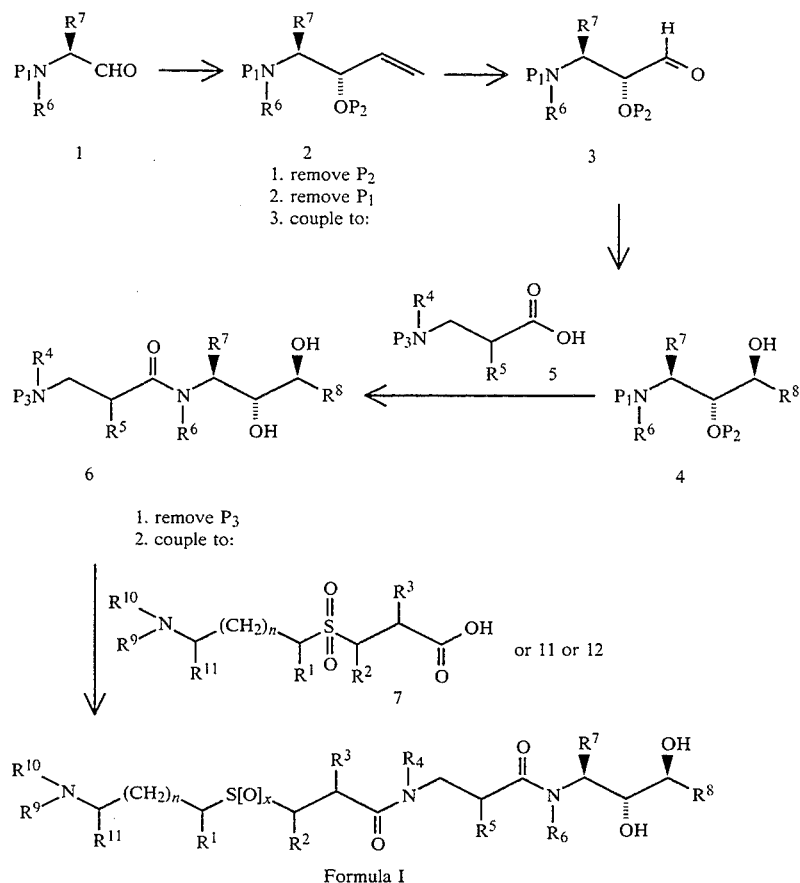

wherein $R^1$ through $R^{11}$, x and n are as defined above.

A suitably protected amino aldehyde 1 is treated with a Grignard reagent or other organometallic reagent, preferably vinylmagnesium bromide, to obtain the vinyl carbinol 2. This material, suitably protected, is oxidized, preferably with ozone, followed by dimethyl sulfide or zinc treatment, to give intermediate 3. The preceding process is exemplified in Hanson et al, *J. Org. Chem.*, 50, 5399 (1985). This aldehyde is reacted with an organometallic reagent such as isobutylmagnesium chloride to give intermediate 4. Compound 4 is deprotected then coupled, using standard amide/peptide coupling methodology to protected β-amino acid derivatives 5 to give compound 6. These standard coupling procedures such as the carbodiimide, active ester (N-hydroxysuccinimide), and mixed carbonic anhydride methods are shown in Benoiton et al, *J. Org. Chem.*, 48, 2939 (1983) and Bodansky et al, "Peptide Synthesis", Wiley (1976). Intermediate 6 is then deprotected, then coupled to intermediate 7 or 11 or 12 using the standard amide/peptide coupling methodology, to give compounds of Formula I. Suitable protecting groups may be selected from among those reviewed by R. Geiger in "The Peptides", Academic Press, N.Y. vol. 2 (1979). For example, $P_1$ or $P_3$ may be Boc or Cbz; $P_2$ may be a typical oxygen protective group such as acetyl or t-butyldimethylsilyl.

Synthetic Scheme 2

Preparation of 7:

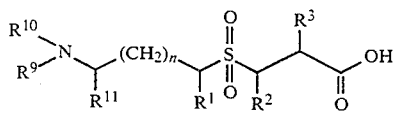

7

-continued
Synthetic Scheme 2

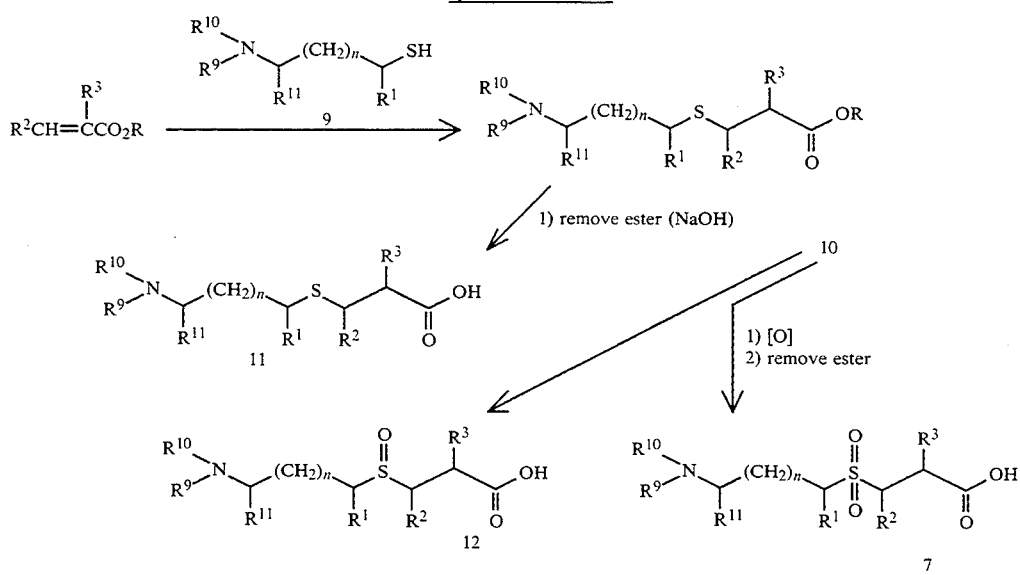

wherein $R^1$ through $R^3$, $R^9$ through $R^{11}$ and n are as defined above and R is lower alkyl or benzyl.

Intermediate 7 may be prepared according to Synthetic Scheme 2. The addition of thiol 9 to an acrylic ester 8 in the presence of base catalysts such as sodium hydroxide, triethylamine or benzyltrimethylammonium hydroxide, afforded the α,β disubstituted propanoic ester 10. Compound 10 is converted into its corresponding propanoic acid 11 via alkaline hydrolysis. Compound 10 may be converted to either sulfone 7 or sulfoxide 12 via a two step process: oxidation with 3-chloroperbenzoic acid (for 12) or potassium peroxomonsulfate (for 7), followed by alkaline hydrolysis or hydrogenolysis (when R=benzyl).

Abbreviations: $P_1$ is an N-protecting group; $P_2$ is H or an oxygen protecting group; $P_3$ is an N-protecting group.

The following Steps 1–14 constitute specific exemplification of methods to prepare starting materials and intermediates embraced by the foregoing generic synthetic schemes. Those skilled in the art will readily understand that known variations of the conditions and processes of the following preparative procedures can be used to prepare the compounds of Steps 1–14. All temperatures expressed are in degrees Centigrade. Compound of Example 1 was prepared by using the procedures described in the following Steps 1–14:

Step 1: Preparation of (2R,3S)-N-[(tert-Butyloxy)carbonyl]-3-amino-2-acetoxy-4-phenylbutanal Ozone/oxygen was bubbled at −70° C. into a solution of (3 S,4S)-N-[(tert-Butyloxy)carbonyl]-4-amino-3-acetoxy-5-phenylpentene (2.55 g, 8.0 mmol) [prepared by the method of Hanson et al, *J. Org. Chem.*, 50, 5399 (1985)] in 100 mL of methylene chloride until a deep blue color persisted. Oxygen was introduced until the blue color completely faded, then 3.0 mL of $Me_2S$ was added and the solution was allowed to warm to 0°–5° C. and stand overnight. The solvent was removed at 0° C. under vacuum yielding the title compound as a thick yellow oil which was used in the following step without purification.

Step 2: Preparation of (2S,3R,4S)-N-[(tert-Butyloxy)carbonyl]-2-amino-1-phenyl-3,4-dihydroxy-6-methylheptane The oil prepared in Step 1 was dissolved under nitrogen in 100 mL of dry THF and cooled to −70° C. To this solution was added 13 mL (26 mmol) of a 2.0M solution of isobutylmagnesium chloride in ether and the stirred mixture was allowed to warm to room temperature and stir for 2 hrs. After decomposition with $MeOH/H_2O$ the mixture was diluted with ether, washed with saturated $NH_4Cl$ solution twice, then dried and the solvents stripped off under vacuum. The residue was allowed to stand overnight in 80% MeOH—$H_2O$ containing excess ammonium hydroxide. The MeOH was stripped off and the mixture was extracted with ether. These extracts were combined, washed with water, dilute $KHSO_4$, then dried and evaporated to give 2.36 g of a yellow glass which crystallized from 50 mL of pentane on standing overnight. The yellow-white powder obtained was recrystallized from ether-hexane and furnished the title compound (0.41 g) as white, hairy needles, mp 134°–136° C., Rf (ether): single spot, 0.6. By chromatography of the mother liquors and crystallization of the appropriate fractions, an additional 0.22 g of product, mp 138°–139° C., was obtained. Anal: Calcd. for $C_{19}H_{31}NO_4$ (337.45): C, 67.62; H, 9.26; N, 4.15. Found: C, 67.51; H, 9.43; N, 4.24.

Step 3: Preparation of (2S,3R,4S)-N-[(tert-Butyloxy)carbonyl]-2-amino-1-cyclohexyl-3,4-dihydroxy-6-methylheptane The diol of Step 2, 0.27 g, was reduced in MeOH with 60 psi $H_2$ at 60° C. in 3 hrs using 5% Rh/C catalyst. After filtering, the solvent was stripped off and the white crystals were recrystallized from $CH_2Cl_2$-hexane to furnish tiny needles of the title compound, 0.19 g, mp 126°–128° C.; further recrystallization gave mp 128.5°–129.5° C. Rf (ether): single spot, 0.8. Anal: Calcd. four $C_{19}H_{37}NO_4$ (343.50): C, 66.43; H, 10.86, N, 4.08. Found: C, 66.43; H, 11.01; N, 4.03.

Step 4: Preparation of (2S,3R,4S)-2-amino-1-cyclohexyl-3,4-dihydroxy-6-methylheptane The title compound of Step 3 (10 g) was dissolved 6.9N HCl in dioxane (300 mL). The mixture was stirred for 30 minutes at room temperature. The solvent was removed in vacuo and to the residue was added 5% aqueous sodium hydroxide (30 mL) until a pH of 14 was obtained. This mixture was extracted with ether and the ether extract was washed with water and brine, then the solvent was evaporated to give the title compound (7.3 g, 100% yield). $^1$H NMR: 300 MHz spectrum consistent with proposed structure. Anal: calcd. for $C_{14}H_{29}NO_2$: C, 69.07; H, 12.01; N, 5.78. Found: C, 69.19; H, 12.34; N, 5.78.

Step 5: Preparation of N-Boc-α-(R)-methyl-β-alanineamide of (2S,3R,4S)-2-amino-1-cyclohexyl-3,4-dihydroxy-6-methylheptane To a solution of N-Boc-α-(R,S)-methyl-β-alanine (137 mg, 0.67 mmol) in methylene chloride (4 mL) at −10° C. was added N-methylpiperidine (61 mg, 0.61 mmol) followed by isobutylchloroformate (75 mg, 0.55 mmol). After stirring for 5 min., a solution of the amine of Step 4 in methylene chloride (2 mL) was added. The resulting solution was stirred for 3 hours at −10° C., followed by 2 hours at room temperature at which time a white solid was isolated by filteration (60 mg, 34% yield): Rf=0.3 (5% MeOH/methylene chloride, silica gel); mp 197°-200°; $^1$H NMR (CDCl$_3$): consistent with proposed structure. Anal: Calc'd for $C_{23}H_{44}N_2O_5 + 0.25$ $H_2O$: C, 63.77; H, 10.35; N, 6.46. Found: C, 63.84; H, 10.50; N, 6.45.

Step 6: Preparation of α-(R)-methyl-β-alanineamide of (2S,3R,4S)-2-amino-1-cyclohexyl-3,4-dihydroxy-6-methylheptane The title compound of Step 5 (53 mg, 0.12 mmol) S was stirred with a mixture of trifluoroacetic acid and methanol (9:1, 5 mL). The resulting solution was allowed to stand at room temperature for 20 minutes, then the solvent was evaporated. The resulting oil was stirred for 2 hours with aqueous potassium carbonate (5%, 10 mL). This mixture was then extracted with ethyl acetate which was dried, filtered and evaporated to give the title compound (40 mg, 100%): Rf: 0.10 (5% MeOH/methylene chloride, silica gel). This material was used without further purification.

Step 7: Preparation of ethyl α-methylenebenzenepropanoate

A mixture of of KOH (8.5 g) in ethanol (100 mL) was added at room temperature to benzylmalonic acid diethyl ester (40 g) in ethanol (80 mL) and the whole was stirred at room temperature overnight, then concentrated by evaporation, thereafter water (14 mL) was added and then the mixture was acidified in an ice bath with concentrated hydrochloric acid (12.6 mL). Partitioning between water and ether was carried out, the organic phase was dried and the ether was distilled off. Then, pyridine (26 mL), piperidine (1.22 g) and paraformaldehyde (3.56 g) were added to the residue. The mixture was heated in an oil bath (130°) for 90 minutes, cooled, water (440 mL) were added and extraction was carried out 3 times with n-hexane (150 mL). The combined organic phases were washed successively with water, 1N HCl, water, saturated NaHCO$_3$ solution and brine. The solution was dried (MgSO$_4$) and evaporated to give the title compound as colorless oil (26 g, 85% yield). $^1$H NMR: 300 MHz spectrum consistent with proposed structure.

Step 8: Preparation of α-methylenebenzenepropanoic acid

The ethyl α-methylenebenzenepropanoate of Step 7 (4.6 g, 24.3 mmol) was dissolved in methanol (12 mL) and then reacted with 2N potassium hydroxide (24 mL) solution. The mixture was stirred at room temperature for 4 hours and concentrated by evaporation. The residue was diluted with water and washed with ether. The aqueous layer was acidified to pH 2 with 1N HCl, and then extracted with ethyl acetate. The extracts were dried (Na$_2$SO$_4$) and evaporated to give the title compound as colorless oil (2.8 g, 66% yield). $^1$H NMR: 300 MHz spectrum consistent with proposed structure.

Step 9: Preparation of phenylmethyl α-methylenebenzenepropanoate

The title acid of Step 8 (5.2 g, 30 mmol) was dissolved in dimethylformamide (25 mL) and cooled to 0° C. To this potassium carbonate (5.7 g, 41.48 mmol) was added followed by benzyl bromide (5.7 g, 29.7 mmol). The mixture was stirred at room temperature overnight. The mixture was filtered and the filtrate was diluted with ethyl acetate, washed with 3 times of water, brine. The solution was dried (Na$_2$SO$_4$) and evaporated. The residue was purified by flash chromatography on silica gel, eluting with 90:10 heptane:ethyl acetate to give the pure title compound as yellow oil (4.5 g, 60% yield). $^1$H NMR: 300 MHz spectrum consistent with proposed structure. Anal: calcd. for $C_{17}H_{16}O_2$: C, 80.93; H, 6.39. Found: C, 80.69; H, 6.47.

Step 10: Preparation of phenylmethyl α[[[2-(dimethylamino)ethyl]thio]methyl]benzenepropanoate The oil prepared in Step 9 (1.5 g, 5.95 mmol) was dissolved under argon in methanol (22 mL). To this solution was added 2-dimethylaminoethanethiol hydrochloride (843 mg, 5.95 mmol), piperidine (0.78 mL, 7.85 mmol) and benzyltrimethylammonium hydroxide (0.25 mL, 0.6 mmol), and the mixture was stirred at room temperature for 16 hours. The solvent was removed on a rotary evaporator and then the residue was purified by flash chromatography on silica gel, eluting with 20:1 CH$_2$Cl$_2$:MeOH to give the pure title compound (0.5 g, 24% yield). $^1$H NMR: 300 MHz spectrum consistent with proposed structure. Anal: calcd. for $C_{21}H_{27}NO_2S + 0.2H_2O$: C, 69.85; H, 7.65; N, 3.88. Found: C, 69.58; H, 7.60; N, 3.98.

Step 11: Preparation of phenylmethyl α[[[2-(dimethylamino)ethyl]sulfonyl]methyl]benzenepropanoate The title compound in Step 10 (0.5 g, 1.4 mmol) was dissolved in methanol (7 mL) and, while cooling with ice, oxone (potassium peroxomonosulfate) (1.3 g) in water (6 mL) were added and the whole was stirred at room temperature overnight. The solution was diluted with water and extracted with methylene chloride, and the extracts were dried (Na$_2$SO$_4$) and concentrated by evaporation. The residue was purified by flash chromatography on silica gel, eluting with 20:1 CH$_2$Cl$_2$:MeOH to give pure title compound as white powder (400 mg, 73%). $^1$H NMR: 300 MHz spectrum consistent with proposed structure. Anal: calcd. for $C_{21}H_{27}NO_4S$: C, 64.76; H, 6.99; N, 3.60. Found: C, 64.01; H, 6.88; N, 3.41.

Step 12: Preparation of α-[[[2-(dimethylamino)ethyl]sulfonyl]methyl]benzenepropanoic acid The title compound of Step 11 (150 mg, 0.4 mmol) was debenzylated in ethanol with 5 psi H$_2$ at room temperature for 1.5 hours using 4% Pd/C catalyst. After filtering, the solvent was stripped off to give the title compound as white powder (110 mg, 70% yield). $^1$H NMR: 300 MHz spectrum consistent with proposed structure. Anal: calcd. for $C_{14}H_{21}NO_4S$: C, 56.16; H, 7.07; N, 4.68. Found: C, 5.88; H, 6.99; N, 4.35.

Step 13: Preparation of α-[[[2-(dimethylamino)ethyl]thio]methyl]benzene propanoic acid sodium salt The title compound of Step 10 is dissolved in methanol at room temperature and to this is added 1 molar equivalent of 1N aqueous sodium hydroxide. This solution is allowed to stand for 2–4 hours, then evaporated to dryness to afford the title compound. This material is used without further purification.

Step 14: Preparation of α-[[[2-(diethylamino)ethyl]sulfonyl]methyl]benzene propanoic acid The title compound may be prepared by substituting the 2-dimethylaminoethanethiol hydrochloride in Step 10 with 2-diethylaminoethanethiol hydrochloride and proceeding with Steps 11 and 12 to yield the title acid.

The following working Examples are provided to illustrate synthesis of Compounds 1–24 of the present invention and are not intended to limit the scope thereof. Those skilled in the art will readily understand that known variations of the conditions and processes of the following preparative procedures can be used to prepare the compounds of the Examples. All temperatures expressed are in degrees Centigrade.

EXAMPLE 1

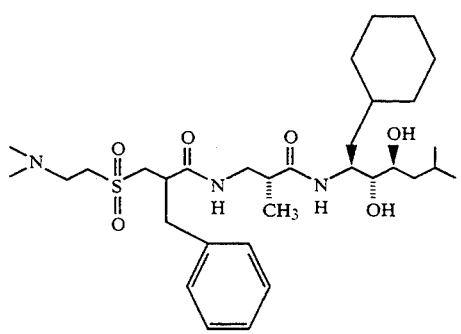

The acid of Step 12 (110 mg, 0.36 mmol) was dissolved at room temperature in a mixture of dimethylformamide (2 mL) and pyridine (0.4 mL) and to this solution was added N,N'-disuccinimidyl carbonate (84 mg, 0.33 mmol) and 4-dimethylaminopyridine (4 mg). The mixture was stirred for 3 hours, and then the title amine of Step 6 (108 mg, 0.33 mmol) was added, followed by diisopropylethylamine (57 mL). This mixture was allowed to stir at room temperature for 16 hours. The solvent was then evaporated and the residue dissolved in ethyl acetate (10 mL). The mixture was washed successively with water, saturated sodium bicarbonate and brine. The solution was dried ($Na_2SO_4$) and evaporated. The residue was purified by flash chromatography on silica gel, eluting with 96:3:1 EtOAc:MeOH:NH$_4$OH to give the title compound as white powder (60 mg, 30% yield). $^1$H NMR: 300 MHz spectrum consistent with proposed structure. Anal: calc'd. for $C_{33}H_{55}N_3O_6S + 0.4H_2O$: C, 62.29; H, 9.11; N, 6.81. Found: C, 62.20; H, 8.86; N, 6.75.

EXAMPLE 2

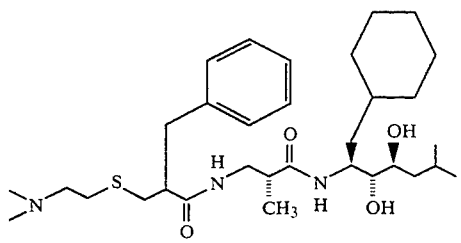

The acid of Step 13 (170 mg, 0.64 mmol) is dissolved at room temperature in a mixture of dimethylformamide (3 mL) and pyridine (0.6 mL) and to this solution is added N,N'-disuccinimidyl carbonate (163 mg, 0.64 mmol) and 4-dimethylaminopyridine (6 mg). The mixture is stirred for 3 hours, and then the title amine of Step 6 (190 mg, 0.5 mmol) is added, followed by diisopropylethylamine (87 mL). This mixture is allowed to stir at room temperature for 16 hours. The solvent is then evaporated and the residue dissolved in ethyl acetate (15 mL). The mixture is washed successively with water, saturated sodium bicarbonate and brine. The solution is dried ($Na_2SO_4$) and evaporated. The residue is purified by flash chromatography on silica gel to give the title compound.

EXAMPLE 3

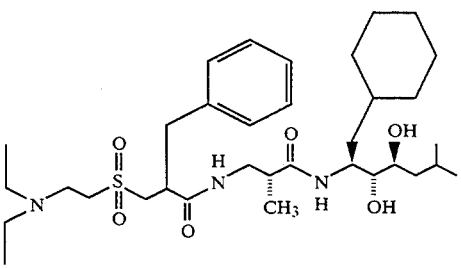

The acid of Step 14 (209 mg, 0.64 mmol) is dissolved at room temperature in a mixture of dimethylformamide (3 mL) and pyridine (0.6 mL) and to this solution is added N,N'-disuccinimidyl carbonate (163 mg, 0.64 mmol) and 4-dimethylaminopyridine (6 mg). The mixture is stirred for 3 hours, and then the title amine of Step 6 (190 mg, 0.5 mmol) is added, followed by diisopropylethylamine (87 mL). This mixture is allowed to stir at room temperature for 16 hours. The solvent is then evaporated and the residue dissolved in ethyl acetate (15 mL). The mixture is washed successively with water, saturated sodium bicarbonate and brine. The solution is dried ($Na_2SO_4$) and evaporated. The residue is purified by flash chromatography on silica gel to give the title compound.

Compounds 4–24, as shown in Table 1 below, may be synthesized by reference to the foregoing specific and general procedures for preparing compounds of Formula I.

TABLE I
| Example Compound No. | Structure |
|---|---|
| 4 | 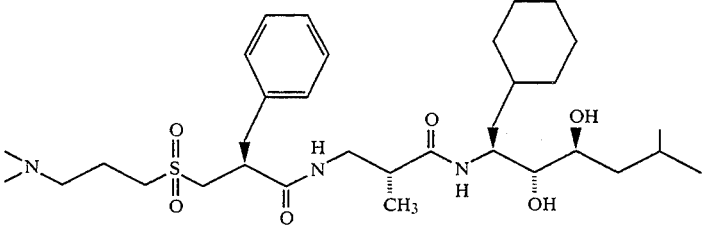 |
| 5 | 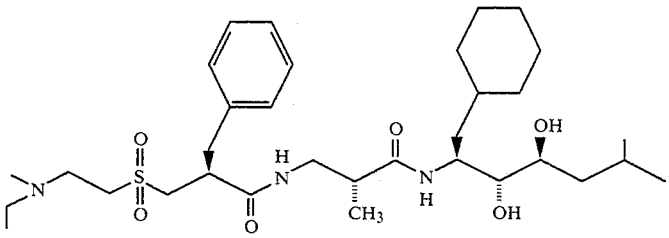 |
| 6 | 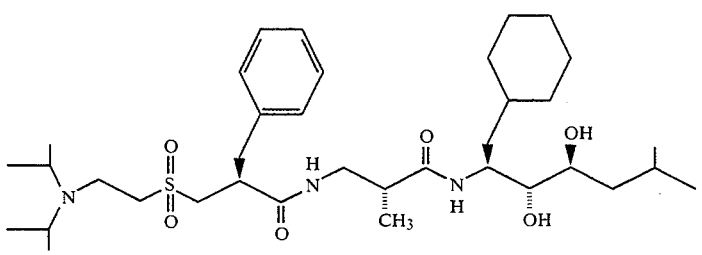 |
| 7 | 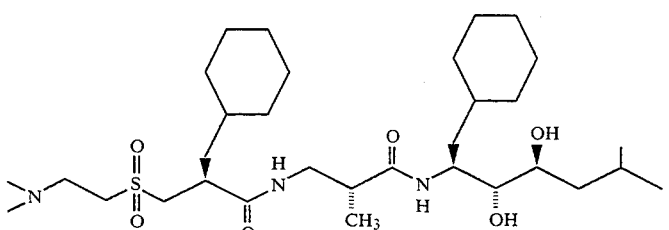 |
| 8 | 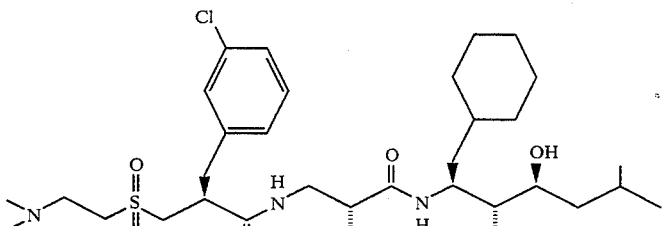 |
| 9 | 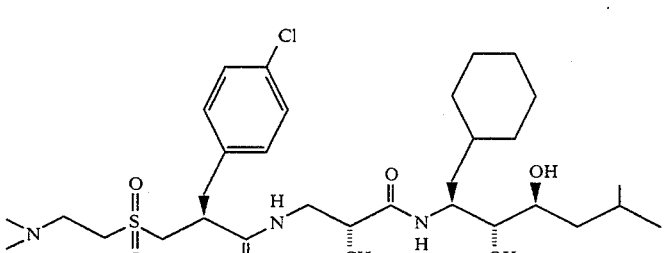 |

TABLE I-continued
| Example Compound No. | Structure |
|---|---|
| 10 | 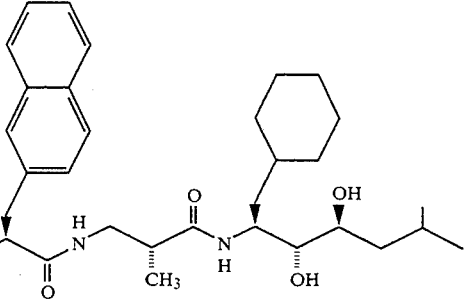 |
| 11 | 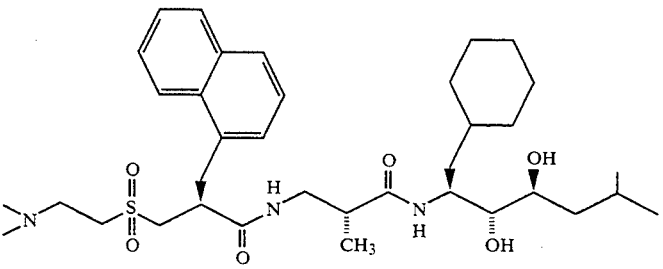 |
| 12 | 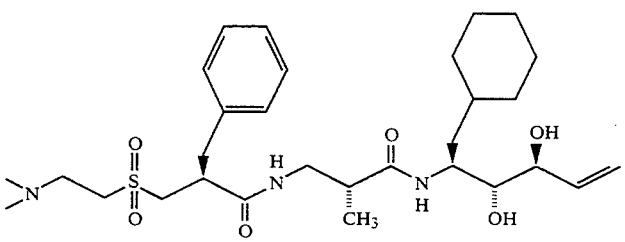 |
| 13 | 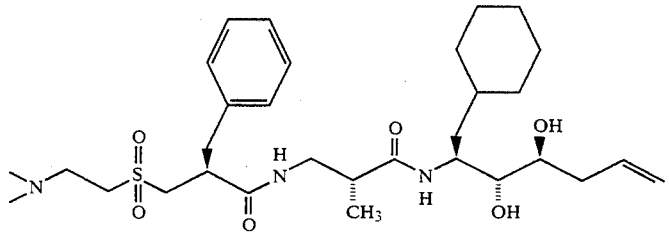 |
| 14 | 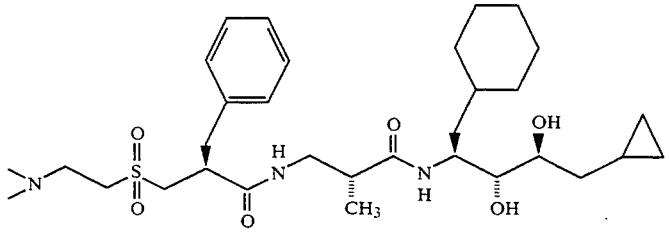 |
| 15 | 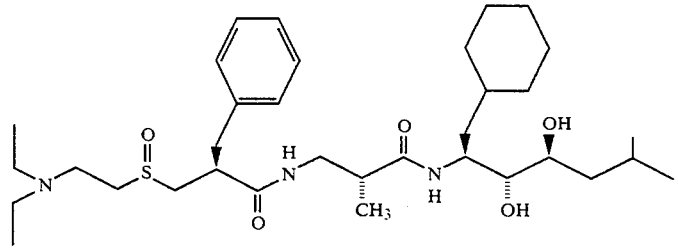 |

TABLE I-continued
| Example Compound No. | Structure |
| --- | --- |
| 16 | 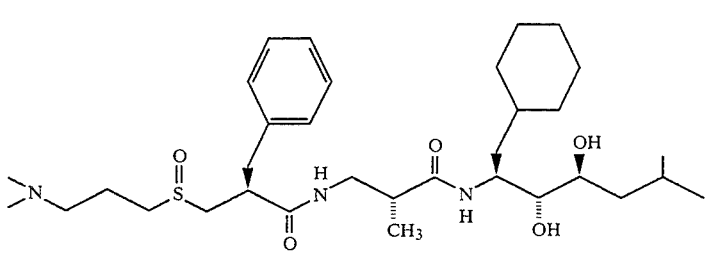 |
| 17 | 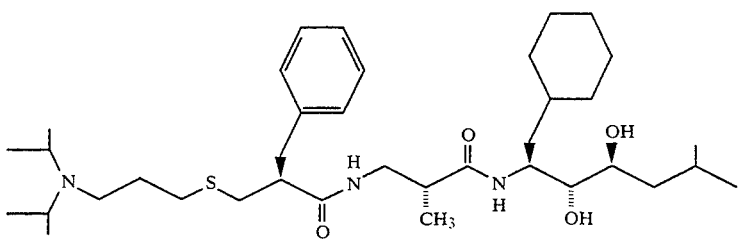 |
| 18 | 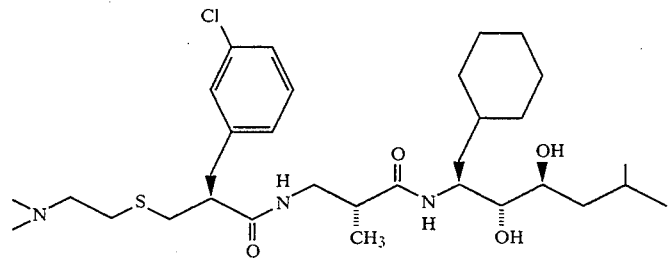 |
| 19 | 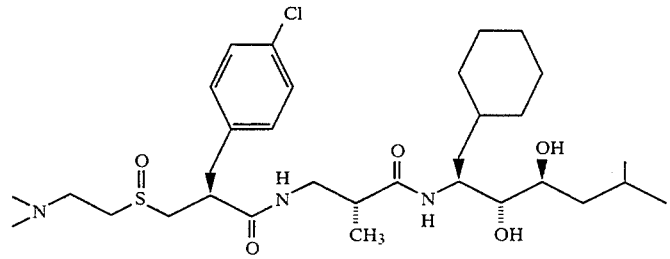 |
| 20 | 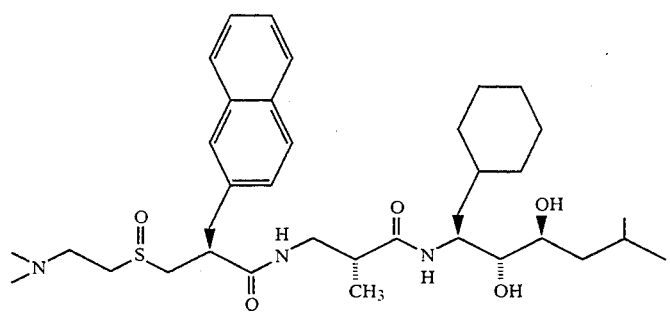 |

TABLE I-continued

| Example Compound No. | Structure |
|---|---|
| 21 | *(structure: dimethylaminoethyl-S-CH2-CH(naphthyl)-C(O)-NH-CH(CH3)-C(O)-NH-CH(CH2-cyclohexyl)-CH(OH)-CH(OH)-CH2-CH(CH3)2)* |
| 22 | *(structure: dimethylaminoethyl-S-CH2-CH(phenyl)-C(O)-NH-CH(CH3)-C(O)-NH-CH(CH2-cyclohexyl)-CH(OH)-CH(OH)-CH=CH2)* |
| 23 | *(structure: dimethylaminoethyl-S(O)-CH2-CH(phenyl)-C(O)-NH-CH(CH3)-C(O)-NH-CH(CH2-cyclohexyl)-CH(OH)-CH(OH)-CH2-CH=CH2)* |
| 24 | *(structure: dimethylaminoethyl-S-CH2-CH(phenyl)-C(O)-NH-CH(CH3)-C(O)-NH-CH(CH2-cyclohexyl)-CH(OH)-CH(OH)-CH2-cyclopropyl)* |

BIOLOGICAL EVALUATION

Human Renin Inhibition in vitro

Compounds of Formula I were evaluated as inhibitors of human renin in an in vitro assay, as follows: This human renin inhibition test has been previously described in detail [Papaioannou et al., *Clinical and Experimental Hypertension*, A7(9), 1243–1257 (1985)]. Human renin was obtained from the National Institute for Biological Standards, London. An incubation mixture was prepared containing the following components: in a total volume of 0.25 mL: 100 mM Tris-acetate buffer at pH 7.4, $25 \times 10^{-6}$ Goldblatt units of renin, 0.05 mL of plasma from human volunteers taking oral contraceptives, 6.0 mM Na-EDTA, 2.4 mM phenylmethyl sulfonyl fluoride, 1.5 mM 8-hydroxyquinoline, 0.4 mg/mL bovine serum albumin (BSA), and 0.024 mg/mL neomycin sulfate. This mixture was incubated for two hours at 37° C. in the presence or absence of renin inhibitors. The produced angiotensin I was determined by radioimmunoassay (New England Nuclear kit). Test compounds to be assayed were dissolved in DMSO and diluted with 100 mM Tris-acetate buffer at pH 7.4 containing 0.5% BSA to the appropriate concentration. The final concentration of organic solvent in the reaction mixture was less than 1%. Control incubations at 37° C. were used to correct for effects of organic solvent on renin activity. The in vitro enzymatic conversion of angiotensinogen to angiotensin I was inhibited by test compounds of the invention. The compound of Example #1 was found to inhibit human renin in vitro at an $IC_{50}$ of 44 nM.

Also embraced within this invention is a class of pharmaceutical compositions comprising one or more compounds of Formula I in association with one or more non-toxic, pharmaceutically acceptable carriers and/or diluents and/or adjuvants (collectively referred to herein as "carrier" materials) and, if desired, other active ingredients. The compounds of the present invention may be administered by any suitable route, preferably in the form of a pharmaceutical composition adapted to such a route, and in a dose effective for the treatment intended. Therapeutically effective doses of the compounds of the present invention required to prevent or arrest the progress of the medical condition are readily ascertained by one of ordinary skill in the art. The compounds and composition may, for example, be administered intravascularly, intraperitoneally, subcutaneously, intramuscularly or topically.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. These may with advantage contain an amount of active ingredient from about 1 to 250 mg, preferably from about 25 to 150 mg. A suitable daily dose for a mammal may vary widely depending on the condition of the patient and other factors. However, a dose of from about 0.1 to 3000 mg/kg body weight, particularly from about 1 to 100 mg/kg body weight, may be appropriate.

The active ingredient may also be administered by injection as a composition wherein, for example, saline, dextrose or water may be used as a suitable carrier. A suitable daily dose is from about 0.1 to 100 mg/kg body weight injected per day in multiple doses depending on the disease being treated. A preferred daily dose would be from about 1 to 30 mg/kg body weight. Compounds indicated for prophylactic therapy will preferably be administered in a daily dose generally in a range from about 0.1 mg to about 100 mg per kilogram of body weight per day. A more preferred dosage will be a range from about 1 mg to about 100 mg per kilogram of body weight. Most preferred is a dosage in a range from about 1 to about 50 mg per kilogram of body weight per day. A suitable dose can be administered, in multiple sub-doses per day. These sub-doses may be administered in unit dosage forms. Typically, a dose or sub-dose may contain from about 1 mg to about 400 mg of active compound per unit dosage form. A more preferred dosage will contain from about 2 mg to about 200 mg of active compound per unit dosage form. Most preferred is a dosage form containing from about 3 mg to about 100 mg of active compound per unit dose.

The dosage regimen for treating a disease condition with the compounds and/or compositions of this invention is selected in accordance with a variety of factors, including the type, age, weight, sex and medical condition of the patient, the severity of the disease, the route of administration, and the particular compound employed, and thus may vary widely.

For therapeutic purposes, the compounds of this invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Although this invention has been described with respect to specific embodiments, the details of these embodiments are not to be construed as limitations.

What is claimed is:

1. A compound of Formula I:

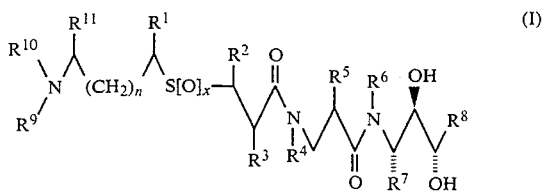

wherein each of $R^1$ and $R^{11}$ is a group independently selected from hydrido, alkyl, alkylaminoalkyl and phenyl; wherein n is a number selected from zero through five, inclusive; wherein x is a number selected from zero, one and two; wherein $R^2$ is selected from hydrido and alkyl; wherein $R^3$ is a group selected from hydrido, cycloalkylalkyl, aralkyl and haloaralkyl; wherein each of $R^4$ and $R^6$ is a group independently selected from hydrido and methyl; wherein $R^5$ is selected from linear and branched alkyl groups containing from one to about four carbon atoms; wherein $R^7$ is a group selected from alkyl, cycloalkylalkyl and aralkyl; wherein $R^8$ is a group selected from hydrido, alkyl, hydroxyalkyl, cycloalkyl, cycloalkylalkyl, alkenyl and haloalkenyl; wherein each of $R^9$ and $R^{10}$ is a group independently selected from hydrido, alkyl, cycloalkyl, cycloalkylalkyl, alkylacyl, aryl, aralkyl, haloaryl and haloaralkyl; and wherein any one of said $R^1$ through $R^{11}$ groups having a substitutable position may be substituted with one or more groups selected from alkyl, hydroxy, hydroxyalkyl, halo, alkoxy, alkoxyalkyl and alkenyl; or a pharmaceutically-acceptable salt thereof.

2. Compound of claim 1 wherein each of $R^1$ and $R^{11}$ is independently selected from hydrido, methyl, ethyl, n-propyl, isopropyl, n-butyl, sec-butyl, iso-butyl, tert-butyl, N,N-dimethylaminomethyl, N,N-diethylaminomethyl, N,N-diethylaminoethyl and phenyl; wherein n is a number selected from zero through four, inclusive; wherein x is a number selected from zero, one and two; wherein $R^2$ is selected from hydrido and alkyl; wherein $R^3$ is selected from hydrido, cycloalkylalkyl, phenylalkyl, halophenylalkyl, naphthylalkyl and halonaphthylalkyl; wherein each of $R^4$ and $R^6$ is independently selected from hydrido and methyl; wherein $R^5$ is selected from methyl, ethyl, n-propyl, isopropyl and n-butyl; wherein $R^7$ is selected from cyclohexylmethyl and benzyl, either one of which may be substituted with one or more groups selected from alkyl, hydroxy and alkoxy; wherein $R^8$ is selected from hydrido, alkyl, cycloalkyl, cycloalkylalkyl, hydroxyalkyl, alkenyl and haloalkenyl; and wherein each of $R^9$ and $R^{10}$ is independently selected from hydrido, alkyl, cycloalkyl, cycloalkylalkyl, alkanoyl, halophenyl, phenylalkyl, halophenylalkyl, naphthyl, halonaphthyl, naphthylalkyl and halonaphthylalkyl; or a pharmaceutically-acceptable salt thereof.

3. Compound of claim 2 wherein each of $R^1$ and $R^{11}$ is independently selected from hydrido, methyl, ethyl, n-propyl and isopropyl; wherein n is a number selected from zero through three, inclusive; wherein x is a number selected from zero, one and two; wherein $R^2$ is selected from hydrido, methyl, ethyl and n-propyl; wherein $R^3$ is selected from hydrido, cyclohexylmethyl, benzyl, phenylethyl, fluorobenzyl, fluorophenylethyl, chlorobenzyl, chlorophenylethyl, naphthylmethyl, naphthylethyl, fluoronaphthylmethyl and chloronaphthylmethyl; wherein each of $R^4$ and $R^6$ is independently selected from hydrido and methyl; wherein $R^5$ is selected from methyl, ethyl, n-propyl and isopropyl; wherein $R^7$ is cyclohexylmethyl; wherein $R^8$ is selected from methyl, ethyl, n-propyl, isopropyl, n-butyl, isobutyl, sec-butyl, tert-butyl, cyclopropyl, cyclobutyl, cyclopropylmethyl, cyclobutylmethyl, cyclohexylmethyl, allyl and vinyl; and wherein each of $R^9$ and $R^{10}$ is independently selected from hydrido, methyl, ethyl, n-propyl, isopropyl, n-butyl, isobutyl, sec-butyl, tert-butyl, cyclopropyl, cyclopropylmethyl, cyclopropylethyl, propylcarbonyl, ethylcarbonyl, methylcarbonyl, phenyl, benzyl, phenylethyl, monochlorophenyl, dichlorophenyl, monofluorophenyl, difluorophenyl, monochlorophenylmethyl, monochlorophenylethyl, dichlorophenylmethyl, dichlorophenylethyl, naphthyl, monofluoronaphthyl, monochloronaphthyl, naphthylmethyl, naphthylethyl, fluoronapthylmethyl and chloronaphthylethyl; or a pharmaceutically-acceptable salt thereof.

4. Compound of claim 3 wherein each of $R^1$ and $R^{11}$ is independently hydrido or methyl; wherein n is a number selected from zero through three, inclusive; wherein x is zero or two; wherein $R^2$ is selected from hydrido, methyl, ethyl and n-propyl; wherein $R^3$ is selected from hydrido, cyclohexylmethyl, benzyl, phenylethyl, phenylpropyl, fluorobenzyl, fluorophenylethyl, chlorobenzyl, chlorophenylethyl, naphthylmethyl, naphthylethyl, fluoronaphthylmethyl and chloronaphthylmethyl; wherein each of $R^4$ and $R^6$ is hydrido; wherein $R^5$ is selected from methyl and ethyl; wherein $R^7$ is cyclohexylmethyl; wherein $R^8$ is selected from ethyl, n-propyl, n-butyl, isobutyl, cyclopropyl, cyclobutyl, cyclopropylmethyl, allyl and vinyl; wherein each of $R^9$ and $R^{10}$ is independently selected from hydrido, methyl, ethyl, n-propyl, isopropyl, cyclopropylmethyl, phenyl, benzyl, monochlorophenyl and dichlorophenyl; or a pharmaceutically-acceptable salt thereof.

5. Compound of claim 5 of Formula II

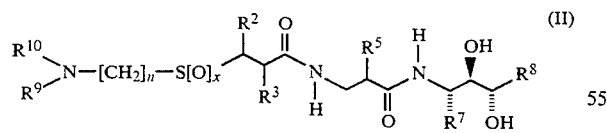

(II)

wherein n is two or three; wherein x is a number selected from zero, one and two; wherein $R^2$ is selected from hydrido, methyl, ethyl and phenyl; wherein $R^3$ is selected from hydrido, cyclohexylmethyl, benzyl, fluorobenzyl, chlorobenzyl, naphthylmethyl, fluoronaphthylmethyl and chloronaphthylmethyl; wherein each of $R^4$ and $R^6$ is hydrido; wherein $R^5$ is methyl; wherein $R^7$ is cyclohexylmethyl; wherein $R^8$ is selected from n-propyl, isobutyl, cyclopropyl, cyclopropylmethyl, allyl and vinyl; wherein each of $R^9$ and $R^{10}$ is independently selected from methyl, ethyl and isopropyl; or a pharmaceutically-acceptable salt thereof.

6. Compound of claim 5 selected from compounds, their tautomers, and the pharmaceutically-acceptable esters thereof, of the group consisting of

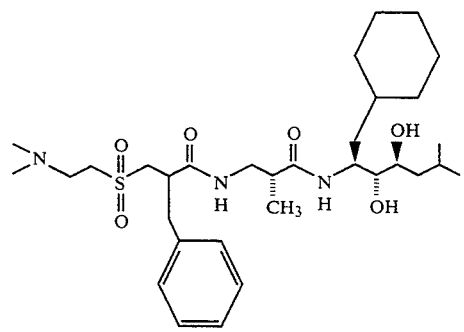

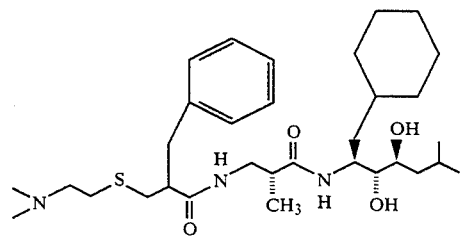

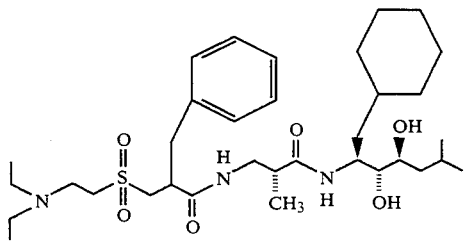

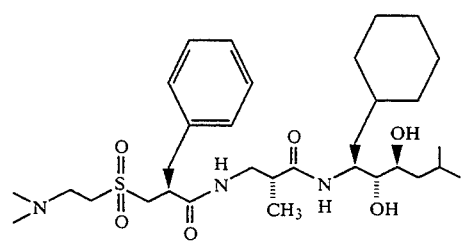

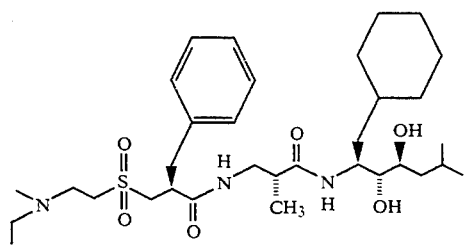

-continued
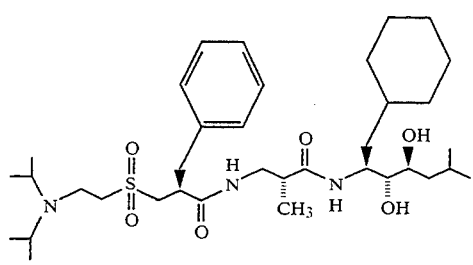
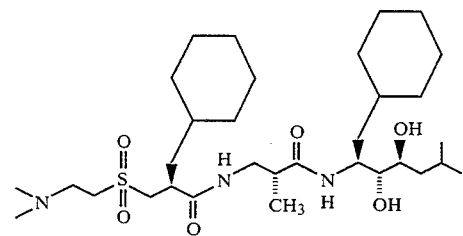
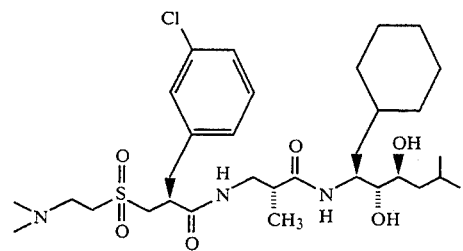
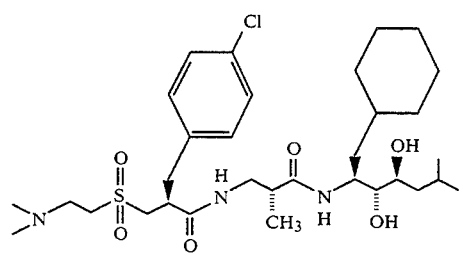
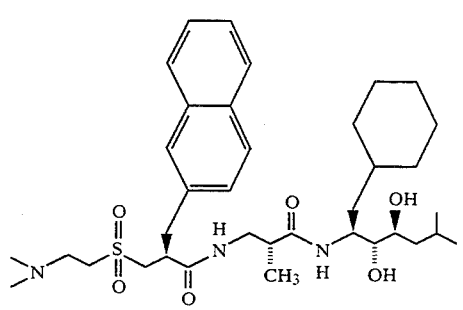
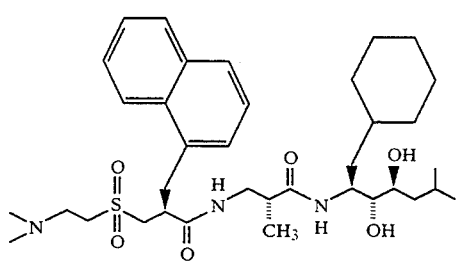
-continued
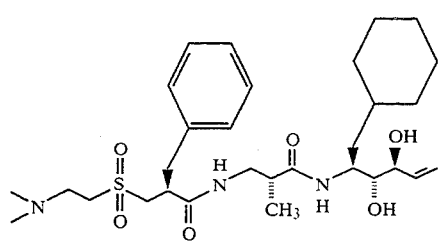
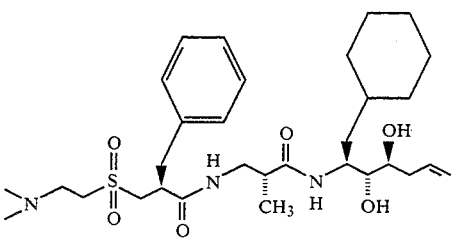
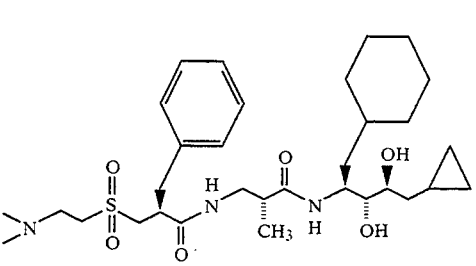
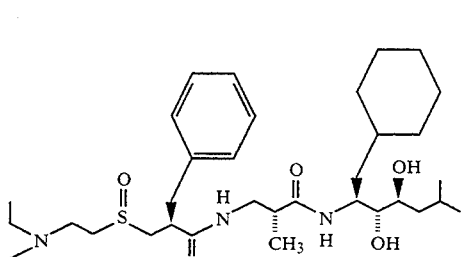
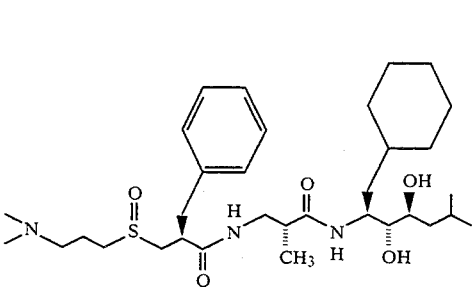
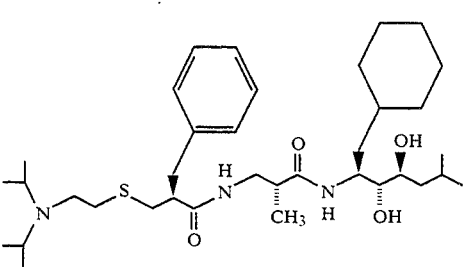

-continued

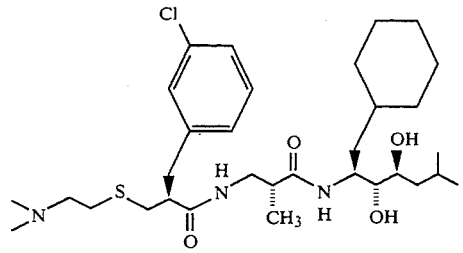

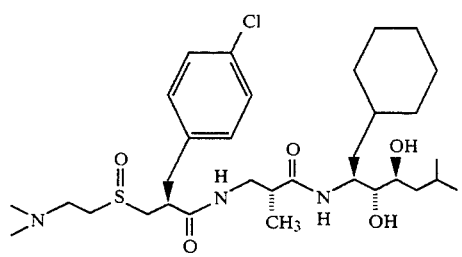

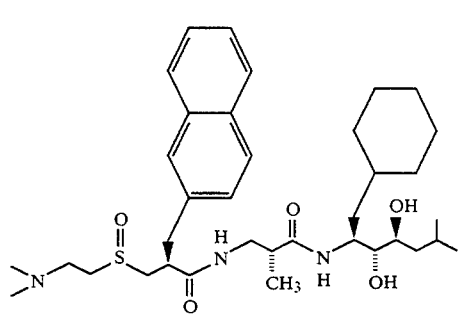

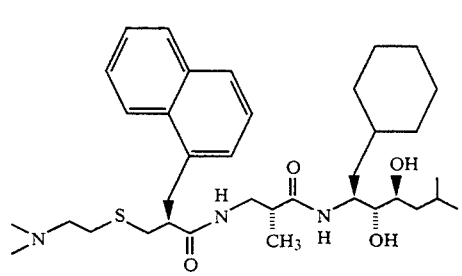

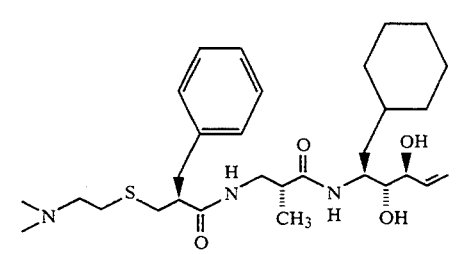

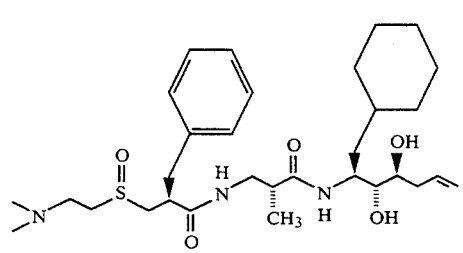

and

-continued

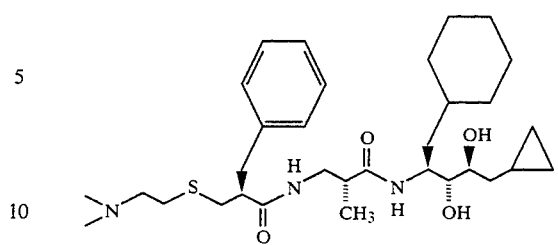

7. Compound of claim 6 which is

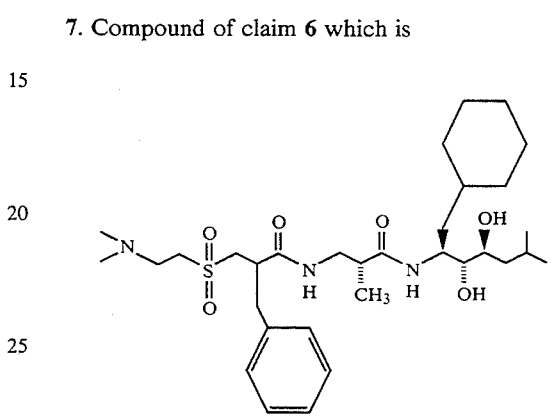

or a pharmaceutically-acceptable salt thereof.
8. Compound of claim 6 which is

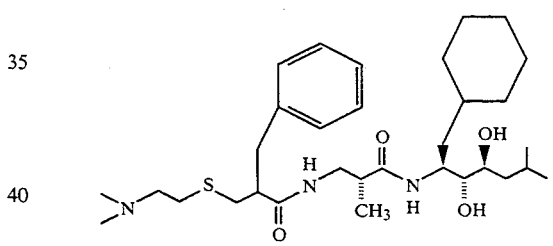

or a pharmaceutically-acceptable salt thereof.
9. Compound of claim 6 which is

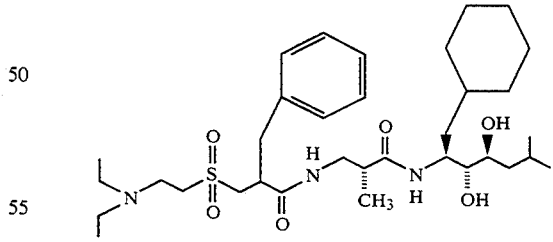

or a pharmaceutically-acceptable salt thereof.
10. A pharmaceutical composition comprising a therapeutically-effective amount of a renin-inhibiting compound and a pharmaceutically-acceptable carrier or diluent, said renin-inhibiting compound selected from a family of compounds of Formula I:

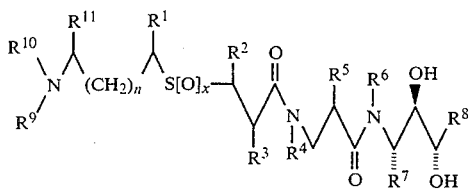 (I)

wherein each of $R^1$ and $R^{11}$ is a group independently selected from hydrido, alkyl, alkylaminoalkyl and phenyl; wherein n is a number selected from zero through five, inclusive; wherein x is a number selected from zero, one and two; wherein $R^2$ is selected from hydrido and alkyl; wherein $R^3$ is a group selected from hydrido, cycloalkylalkyl, aralkyl and haloaralkyl; wherein each of $R^4$ and $R^6$ is a group independently selected from hydrido and methyl; wherein $R^5$ is selected from linear and branched alkyl groups containing from one to about four carbon atoms; wherein $R^7$ is a group selected from alkyl, cycloalkylalkyl and aralkyl; wherein $R^8$ is a group selected from hydrido, alkyl, hydroxyalkyl, cycloalkyl, cycloalkylalkyl, alkenyl and haloalkenyl; wherein each of $R^9$ and $R^{10}$ is a group independently selected from hydrido, alkyl, cycloalkyl, cycloalkylalkyl, alkylacyl, aryl, aralkyl, haloaryl and haloaralkyl; and wherein any one of said $R^1$ through $R^{11}$ groups having a substitutable position may be substituted with one or more groups selected from alkyl, hydroxy, hydroxyalkyl, halo, alkoxy, alkoxyalkyl and alkenyl; or a pharmaceutically-acceptable salt thereof.

11. The composition of claim 10 wherein each of $R^1$ and $R^{11}$ is independently selected from hydrido, methyl, ethyl, n-propyl, isopropyl, n-butyl, sec-butyl, iso-butyl, tert-butyl, N,N-dimethylaminomethyl, N,N-diethylaminomethyl, N,N-diethylaminoethyl and phenyl; wherein n is a number selected from zero through four, inclusive; wherein x is a number selected from zero, one and two; wherein $R^2$ is selected from hydrido and alkyl; wherein $R^3$ is selected from hydrido, cycloalkylalkyl, phenylalkyl, halophenylalkyl, naphthylalkyl and halonaphthylalkyl; wherein each of $R^4$ and $R^6$ is independently selected from hydrido and methyl; wherein $R^5$ is selected from methyl, ethyl, n-propyl, isopropyl and n-butyl; wherein $R^7$ is selected from cyclohexylmethyl and benzyl, either one of which may be substituted with one or more groups selected from alkyl, hydroxy and alkoxy; wherein $R^8$ is selected from hydrido, alkyl, cycloalkyl, cycloalkylalkyl, hydroxyalkyl, alkenyl and haloalkenyl; and wherein each of $R^9$ and $R^{10}$ is independently selected from hydrido, alkyl, cycloalkyl, cycloalkylalkyl, alkanoyl, halophenyl, phenylalkyl, halophenylalkyl, naphthyl, halonaphthyl, naphthylalkyl and halonaphthylalkyl; or a pharmaceutically-acceptable salt thereof.

12. The composition of claim 11 wherein each of $R^1$ and $R^{11}$ is independently selected from hydrido, methyl, ethyl, n-propyl and isopropyl; wherein n is a number selected from zero through three, inclusive; wherein x is a number selected from zero, one and two; wherein $R^2$ is selected from hydrido, methyl, ethyl and n-propyl; wherein $R^3$ is selected from hydrido, cyclohexylmethyl, benzyl, phenylethyl, fluorobenzyl, fluorophenylethyl, chlorobenzyl, chlorophenylethyl, naphthylmethyl, naphthylethyl, fluoronaphthylmethyl and chloronaphthylmethyl; wherein each of $R^4$ and $R^6$ is independently selected from hydrido and methyl; wherein $R^5$ is selected from methyl, ethyl, n-propyl and isopropyl; wherein $R^7$ is cyclohexylmethyl; wherein $R^8$ is selected from methyl, ethyl, n-propyl, isopropyl, n-butyl, isobutyl, sec-butyl, tert-butyl, cyclopropyl, cyclobutyl, cyclopropylmethyl, cyclobutylmethyl, cyclohexylmethyl, allyl and vinyl; and wherein each of $R^9$ and $R^{10}$ is independently selected from hydrido, methyl, ethyl, n-propyl, isopropyl, n-butyl, isobutyl, sec-butyl, tert-butyl, cyclopropyl, cyclopropylmethyl, cyclopropylethyl, propylcarbonyl, ethylcarbonyl, methylcarbonyl, phenyl, benzyl, phenylethyl, monochlorophenyl, dichlorophenyl, monofluorophenyl, difluorophenyl, monochlorophenylmethyl, monochlorophenylethyl, dichlorophenylmethyl, dichlorophenylethyl, naphthyl, monofluoronaphthyl, monochloronaphthyl, naphthylmethyl, naphthylethyl, fluoronapthylmethyl and chloronaphthylethyl; or a pharmaceutically-acceptable salt thereof.

13. The composition of claim 12 wherein each of $R^1$ and $R^{11}$ is independently hydrido or methyl; wherein n is a number selected from zero through three, inclusive; wherein x is zero or two; wherein $R^2$ is selected from hydrido, methyl, ethyl and n-propyl; wherein $R^3$ is selected from hydrido, cyclohexylmethyl, benzyl, phenylethyl, phenylpropyl, fluorobenzyl, fluorophenylethyl, chlorobenzyl, chlorophenylethyl, naphthylmethyl, naphthylethyl, fluoronaphthylmethyl and chloronaphthylmethyl; wherein each of $R^4$ and $R^6$ is hydrido; wherein $R^5$ is selected from methyl and ethyl; wherein $R^7$ is cyclohexylmethyl; wherein $R^8$ is selected from ethyl, n-propyl, n-butyl, isobutyl, cyclopropyl, cyclobutyl, cyclopropylmethyl, allyl and vinyl; wherein each of $R^9$ and $R^{10}$ is independently selected from hydrido, methyl, ethyl, n-propyl, isopropyl, cyclopropylmethyl, phenyl, benzyl, monochlorophenyl and dichlorophenyl; or a pharmaceutically-acceptable salt thereof.

14. The composition of claim 13 wherein said renin-inhibiting compound is of Formula II:

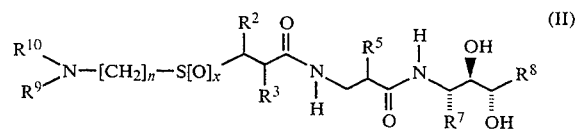 (II)

wherein n is two or three; wherein x is a number selected from zero, one and two; wherein $R^2$ is selected from hydrido, methyl, ethyl and phenyl; wherein $R^3$ is selected from hydrido, cyclohexylmethyl, benzyl, fluorobenzyl, chlorobenzyl, naphthylmethyl, fluoronaphthylmethyl and chloronaphthylmethyl; wherein $R^7$ is cyclohexylmethyl; wherein $R^5$ is methyl; wherein $R^8$ is selected from n-propyl, isobutyl, cyclopropyl, cyclopropylmethyl, allyl and vinyl; wherein each of $R^9$ and $R^{10}$ is independently selected from methyl, ethyl and isopropyl; or a pharmaceutically-acceptable salt thereof.

15. The composition of claim 14 wherein said renin-inhibiting compound is

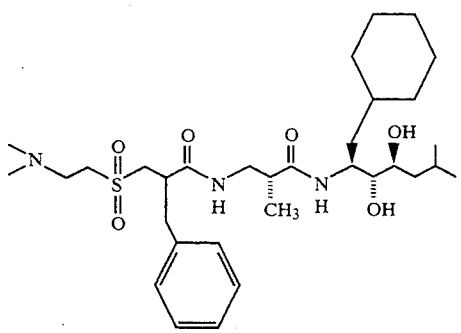

or a pharmaceutically-acceptable salt thereof.

16. The composition of claim 14 wherein said renin-inhibiting compound is

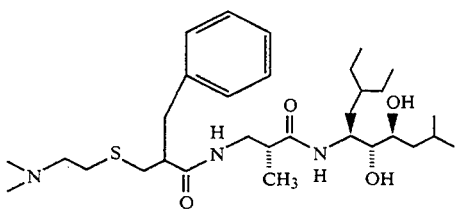

or a pharmaceutically-acceptable salt thereof.

17. The composition of claim 14 wherein said renin-inhibiting compound is

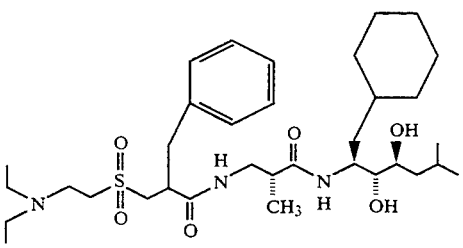

or a pharmaceutically-acceptable salt thereof.

18. A therapeutic method for treating a circulatory-related disorder, said method comprising administering to a hypertensive patient a therapeutically-effective amount of a compound of Formula I:

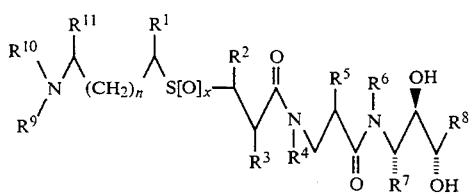

wherein each of $R^1$ and $R^{11}$ is a group independently selected from hydrido, alkyl, alkylaminoalkyl and phenyl; wherein n is a number selected from zero through five, inclusive; wherein x is a number selected from zero, one and two; wherein $R^2$ is selected from hydrido and alkyl; wherein $R^3$ is a group selected from hydrido, cycloalkylalkyl, aralkyl and haloaralkyl; wherein each of $R^4$ and $R^6$ is a group independently selected from hydrido and methyl; wherein $R^5$ is selected from linear and branched alkyl groups containing from one to about four carbon atoms; wherein $R^7$ is a group selected from alkyl, cycloalkylalkyl and aralkyl; wherein $R^8$ is a group selected from hydrido, alkyl, hydroxyalkyl, cycloalkyl, cycloalkylalkyl, alkenyl and haloalkenyl; wherein each of $R^9$ and $R^{10}$ is a group independently selected from hydrido, alkyl, cycloalkyl, cycloalkylalkyl, alkylacyl, aryl, aralkyl, haloaryl and haloaralkyl; and wherein any one of said $R^1$ through $R^{11}$ groups having a substitutable position may be substituted with one or more groups selected from alkyl, hydroxy, hydroxyalkyl, halo, alkoxy, alkoxyalkyl and alkenyl; or a pharmaceutically-acceptable salt thereof.

19. The method of claim 18 wherein each of $R^1$ and $R^{11}$ is independently selected from hydrido, methyl, ethyl, n-propyl, isopropyl, n-butyl, sec-butyl, iso-butyl, tert-butyl, N,N-dimethylaminomethyl, N,N-diethylaminomethyl, N,N-diethylaminoethyl and phenyl; wherein n is a number selected from zero through four, inclusive; wherein x is a number selected from zero, one and two; wherein $R^2$ is selected from hydrido and alkyl; wherein $R^3$ is selected from hydrido, cycloalkylalkyl, phenylalkyl, halophenylalkyl, naphthylalkyl and halonaphthylalkyl; wherein each of $R^4$ and $R^6$ is independently selected from hydrido and methyl; wherein $R^5$ is selected from methyl, ethyl, n-propyl, iso-propyl and n-butyl; wherein $R^7$ is selected from cyclohexylmethyl and benzyl, either one of which may be substituted with one or more groups selected from alkyl, hydroxy and alkoxy; wherein $R^8$ is selected from hydrido, alkyl, cycloalkyl, cycloalkylalkyl, hydroxyalkyl, alkenyl and haloalkenyl; and wherein each of $R^9$ and $R^{10}$ is independently selected from hydrido, alkyl, cycloalkyl, cycloalkylalkyl, alkanoyl, halophenyl, phenylalkyl; halophenylalkyl, naphthyl, halonaphthyl, naphthylalkyl and halonaphthylalkyl; or a pharmaceutically-acceptable salt thereof.

20. The method of claim 19 wherein each of $R^1$ and $R^{11}$ is independently selected from hydrido, methyl, ethyl, n-propyl and isopropyl; wherein n is a number selected from zero through three, inclusive; wherein x is a number selected from zero, one and two; wherein $R^2$ is selected from hydrido, methyl, ethyl and n-propyl; wherein $R^3$ is selected from hydrido, cyclohexylmethyl, benzyl, phenylethyl, fluorobenzyl, fluorophenylethyl, chlorobenzyl, chlorophenylethyl, naphthylmethyl, naphthylethyl, fluoronaphthylmethyl and chloronaphthylmethyl; wherein each of $R^4$ and $R^6$ is independently selected from hydrido and methyl; wherein $R^5$ is selected from methyl, ethyl, n-propyl and iso-propyl; wherein $R^7$ is cyclohexylmethyl; wherein $R^8$ is selected from methyl, ethyl, n-propyl, isopropyl, n-butyl, isobutyl, sec-butyl, tert-butyl, cyclopropyl, cyclobutyl, cyclopropylmethyl, cyclobutylmethyl, cyclohexylmethyl, allyl and vinyl; and wherein each of $R^9$ and $R^{10}$ is independently selected from hydrido, methyl, ethyl, n-propyl, isopropyl, n-butyl, isobutyl, sec-butyl, tert-butyl, cyclopropyl, cyclopropylmethyl, cyclopropylethyl, propylcarbonyl, ethylcarbonyl, methylcarbonyl, phenyl, benzyl, phenylethyl, monochlorophenyl, dichlorophenyl, monofluorophenyl, difluorophenyl, monochlorophenylmethyl, monochlorophenylethyl, dichlorophenylmethyl, dichlorophenylethyl, naphthyl, monofluoronaphthyl, monochloronaphthyl, naphthylmethyl, naphthylethyl, fluoronapthylmethyl and chloronaphthylethyl; or a pharmaceutically-acceptable salt thereof.

21. The method of claim 20 wherein each of $R^1$ and $R^{11}$ is independently hydrido or methyl; wherein n is a number selected from zero through three, inclusive; wherein x is zero or two; wherein $R^2$ is selected from hydrido, methyl, ethyl and n-propyl; wherein $R^3$ is selected from hydrido, cyclohexylmethyl, benzyl, phenylethyl, phenylpropyl, fluorobenzyl, fluorophenylethyl, chlorobenzyl, chlorophenylethyl, naphthylmethyl, naphthylethyl, fluoronaphthylmethyl and chloronaphthylmethyl; wherein each of $R^4$ and $R^6$ is hydrido; wherein $R^5$ is selected from methyl and ethyl; wherein $R^7$ is cyclohexylmethyl; wherein $R^8$ is selected from ethyl, n-propyl, n-butyl, isobutyl, cyclopropyl, cyclobutyl, cyclopropylmethyl, allyl and vinyl; wherein each of $R^9$ and $R^{10}$ is independently selected from hydrido, methyl, ethyl, n-propyl, isopropyl, cyclopropylmethyl, phenyl, benzyl, monochlorophenyl and dichlorophenyl; or a pharmaceutically-acceptable salt thereof.

22. The method of claim 21 wherein said compound is of Formula II:

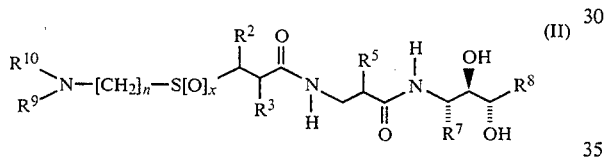

wherein n is two or three; wherein x is a number selected from zero, one and two; wherein $R^2$ is selected from hydrido, methyl, ethyl and phenyl; wherein $R^3$ is selected from hydrido, cyclohexylmethyl, benzyl, fluorobenzyl, chlorobenzyl, naphthylmethyl, fluoronaphthylmethyl and chloronaphthylmethyl; wherein each of $R^4$ and $R^6$ is hydrido; wherein $R^5$ is methyl; wherein $R^7$ is cyclohexylmethyl; wherein $R^8$ is selected from n-propyl, isobutyl, cyclopropyl, cyclopropylmethyl, allyl and vinyl; wherein each of $R^9$ and $R^{10}$ is independently selected from methyl, ethyl and isopropyl; or a pharmaceutically-acceptable salt thereof.

23. The method of claim 22 wherein said compound is

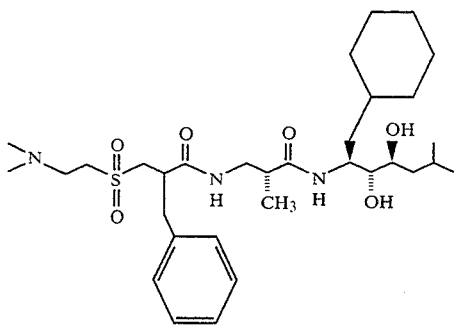

or a pharmaceutically-acceptable salt thereof.

24. The method of claim 22 wherein said compound is

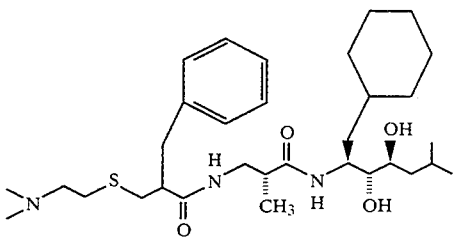

or a pharmaceutically-acceptable salt thereof.

25. The method of claim 22 wherein said compound is

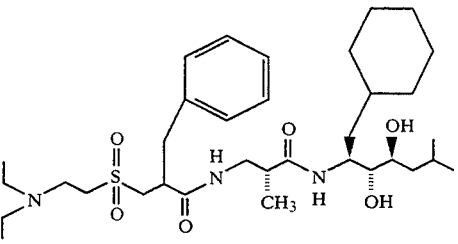

or a pharmaceutically-acceptable salt thereof.

26. The method of claim 18 wherein said circulatory-related disorder is a cardiovascular disorder.

27. The method of claim 26 wherein said cardiovascular disorder is a hypertension.

28. The method of claim 26 wherein said cardiovascular disorder is congestive heart failure.

29. The method of claim 18 wherein said circulatory-related disorder is glaucoma.

30. The method of claim 18 wherein said circulatory-related disorder is renal failure.

* * * * *